United States Patent [19]

Bisagni et al.

[11] Patent Number: 5,091,388
[45] Date of Patent: Feb. 25, 1992

[54] PYRIDOBENZOINDOLE DERIVATIVES, THEIR PREPARATION AND COMPOSITIONS WHICH CONTAIN THEM

[75] Inventors: Emile Bisagni, Orsay; Chi-Hung Nguyen, Massy, both of France

[73] Assignee: Rhone-Poulenc Sante, Antony Cedex, France

[21] Appl. No.: 533,416

[22] Filed: Jun. 5, 1990

[30] Foreign Application Priority Data

Jun. 6, 1989 [FR] France .................... 89 07450
Apr. 25, 1990 [FR] France .................... 90 05059

[51] Int. Cl.$^5$ .................. A61K 31/435; C07D 471/04; C07D 221/00; C07D 209/00
[52] U.S. Cl. ........................ 514/285; 546/70
[58] Field of Search ............ 546/70; 514/285

[56] References Cited

FOREIGN PATENT DOCUMENTS 239476 9/1987 European Pat. Off. .............. 546/70

OTHER PUBLICATIONS

Nguyen et al., J. Med. Chem., May 1990, 33 1519–1528.

Lee et al., Heterocycles 16(7) 1981, pp. 1081 to 1084.

Primary Examiner—Mukund J. Shah
Assistant Examiner—E. C. Ward
Attorney, Agent, or Firm—Morgan & Finnegan

[57] ABSTRACT

New pyridobenzoindole derivatives of general formula (I), in which R is H or alkyl (1 or 2 C), alk is straight or branched alkylene (2 to 4 C), $R_1$ denotes a hydrogen atom or an alkyl radical (1 or 2 C), $R_2$ denotes a hydroxy or methoxy radical, and $R_3$ is methyl or ethyl and their addition salts with acids, useful as antitumor agents.

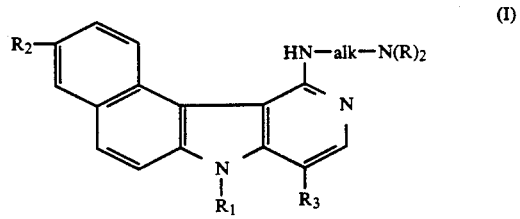

6 Claims, No Drawings

PYRIDOBENZOINDOLE DERIVATIVES, THEIR PREPARATION AND COMPOSITIONS WHICH CONTAIN THEM

FIELD OF THE INVENTION

The present invention relates to new pyridobenzoindole derivatives of general formula:

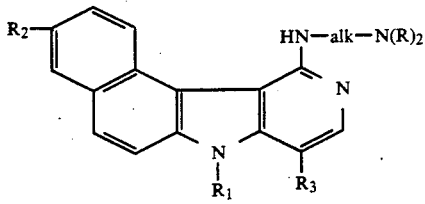
(I)

if appropriate their hydrates, their addition salts with acids, their preparation and pharmaceutical compositions which contain them.

BACKGROUND OF THE INVENTION

In European Patent application 239,476 there were described γ-carboline derivatives of general formula:

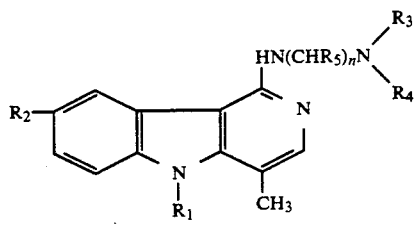

in which $R_1$ and $R_5$ are, among others, hydrogen atoms, $R_2$ may denote a hydrogen atom or a hydroxyl or alkoxy radical, $R_3$ and $R_4$ are especially alkyl radicals and n equals 2 to 4, which exhibit an antitumor activity.

Furthermore, other pyridoindole derivatives have been described in the literature by C. Ducrocq et al., J. Het. Chem., 12 (5), 963 (1975) or by Ch. S. Lee et al., Heterocycles, 16 (7), 1081 (1981), but no therapeutic activity is mentioned.

DETAILED DESCRIPTION OF THE INVENTION

The new pyridobenzoindole derivatives of general formula (I) in which:

R denotes a hydrogen atom or an alkyl radical containing 1 or 2 carbon atoms, alk denotes a straight or branched alkylene radical containing 2 to 4 carbon atoms, $R_1$ denotes a hydrogen atom or an alkyl radical containing 1 or 2 carbon atoms, $R_2$ denotes a hydroxyl or methoxy radical, and $R_3$ denotes an alkyl radical containing 1 or 2 carbon atoms, exhibit particularly advantageous antitumor properties.

According to the invention, the products of general formula (I) can be obtained from the chloro derivative of general formula:

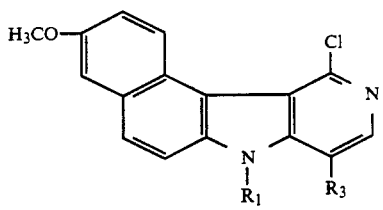
(II)

in which $R_1$ is defined as above, by the action of an amine of general formula:

$$H_2N\text{-alk-}N(R)_2 \quad \text{(III)}$$

in which alk and R are defined as above, followed where appropriate by the conversion of the methoxylated product thus obtained, of general formula

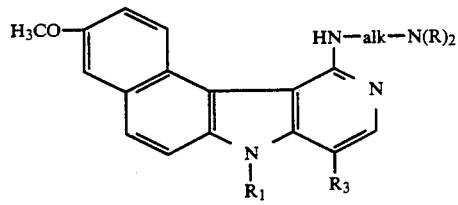
(Ia)

in which R, $R_1$, $R_3$ and alk are defined as above, a 9-hydroxypyrido[4,3-b]benzo[e]indole derivative.

The reaction of the amine of general formula (III) with the chloro derivative of general formula (II) is carried out in the presence of an excess of amine, preferably under nitrogen, optionally in an inert organic solvent, or without solvent, at a temperature between the reflux temperature of the reaction mixture and 250° C. (autoclave).

The demethylation is carried out by any known method which does not affect the rest of the molecule.

The chloro derivative of general formula (II) in which $R_1$ is a hydrogen atom can be prepared from the corresponding pyridone, of general formula:

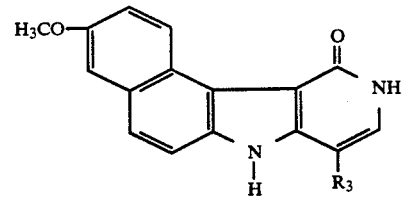
(IV)

in which $R_3$ is defined as above, by the action of a chlorinating agent.

The operation is generally carried out by means of a chlorinating agent chosen from phosphorus oxychloride or halogenated phosphorus derivatives in the presence of a tertiary base (for example diethylaniline or dimethylaniline) in an organic solvent such as a nitrile (for example acetonitrile), at a temperature of between 75 and 90° C. (reflux temperature of the reaction mixture).

The reaction is preferably carried out under nitrogen.

The product of general formula (II) in which $R_1$ is an alkyl radical can be obtained by alkylation of the product in which $R_1$ is a hydrogen atom, for example by the action of the suitable halogen derivative, in the presence of potassium carbonate.

The product of formula (IV) can be prepared from the hydrazone of general formula:

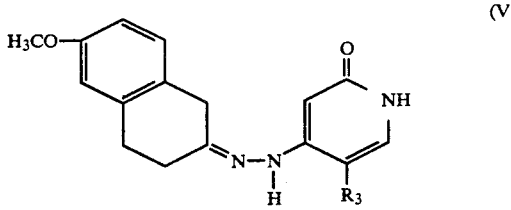

(V)

in which R₃ is defined as above, using a thermal Fisher reaction, by analogy with the method described by C.H. Nguyen and E. Bisagni, Tetrahedron, 42 (8), 2203 (1986).

The hydrazone of general formula (V) is prepared by condensation of 4-hydrazino-5-methyl(or ethyl)-1H-2-pyridone with 6-methoxy-2-tetralone. The reaction is generally carried out in an organic solvent such as an alcohol (for example ethanol) at the reflux temperature of the reaction mixture.

6-Methoxytetralone can be obtained according to the method described in J. Am. Chem. Soc., 82, 2573 (1960).

4-Hydrazino-5-methyl-1H-2-pyridone can be prepared according to the method described by C.H. Nguyen and E. Bisagni, Tetrahedron, 42 (8), 2203 (1986).

The pyridobenzoindole derivatives of general formula (I) can be purified by crystallization or by chromatography.

The new pyridobenzoindole derivatives according to the invention can be converted into addition salts with acids, by the action of an acid in an organic solvent. The salt precipitates, optionally after concentration of its solution; it is isolated by filtration or decanting.

As pharmaceutically acceptable salts there may be mentioned addition salts with inorganic acids such as hydrochlorides, hydrobromides, sulfates, nitrates, phosphates, or with organic acids, such as acetate, propionates, succinates, maleates, fumarates, methanesulphonates, p-toluenesulphonates, isethionates, or substitution derivatives of these compounds.

The pyridobenzoindole derivatives according to the invention and their salts can exist in the form of hydrates; it is obvious that these hydrated forms also come within the scope of the present invention.

In addition, when the symbol alk is a branched alkylene radical the pyridobenzoindole derivatives have isomeric forms. It is obvious that these isomeric forms also come within the scope of the invention.

The derivatives of general formula (I) are particularly advantageous as antitumor agents.

Their antitumor properties have been demonstrated especially at a concentration close to 15 g/disc in the differential cytotoxicity test, according to the technique described by T.H. Corbett et al., Investigational new drug, 4, 207-220 (1986), and on grafted tumors of the mouse, more particularly in leukaemia P388, the products investigated have been found to be active in dosages of between 5 and 20 mg/kg by intraperitoneal route. In the second test, the compound described in example 1 is active at the dose of 5 mg/kg i.v. on i.p. grafted tumors of the mouse.

Their toxicity in the mouse, expressed as their maximum tolerated dose is between 10 and 20 mg/kg by intraperitoneal route.

Because of their antitumor activity, the pyridobenzoindole derivatives which are of particular interest are chiefly those of general formula (I), in which: R is a hydrogen atom or a methyl radical, alk is a straight or branched alkylene radical containing 2 to 4 carbon atoms, R₁ is a hydrogen atom or a methyl radical, R₂ is a hydroxyl radical and R₃ is a methyl or ethyl radical, and their salts and if appropriate their hydrates.

And among these products, those more especially advantageous are the pyridobenzoindole derivatives in which: R is a methyl radical, alk is a straight or branched alkylene radical containing 2 to 4 carbon atoms, R₁ is a hydrogen atom or a methyl radical, R₂ is a hydroxyl radical and R₃ is a methyl radical, and their salts and if appropriate their hydrates.

Especially

[(3-dimethylamino)propyl]-1-amino-9-hydroxy-4-methyl-5H-pyrido [4,3-b]benzo[e]indole and its salts and its hydrated forms, 1-(3-dimethylamino-2-methylpropyl)amino-9-hydroxy-4-methyl-5H-pyrido [4,3-b]benzo[e]indole, and its salts and its hydrated forms.

EXAMPLES

The following examples, given without any limitation being implied, illustrate the present invention.

EXAMPLE 1

1-[(3-Dimethylamino)propyl]amino-9-methoxy-4-methyl-5H-pyrido [4,3-b]benzo[e]indole (8.7 g) is placed in a 500-cc round bottom reaction flask fitted with a stirrer and kept under argon, with hydrobromic acid (220 cc, d = 1.47, 47%).

This mixture, which becomes homogeneous on boiling, is heated under reflux for 4 hours and concentrated to dryness under reduced pressure. The solid residue is dissolved in water (800 cc) and made alkaline with 28% aqueous ammonia (85 cc), added dropwise, to form a resinous precipitate.

Ethyl acetate (800 cc) is added to the resulting mixture. The whole is stirred for 1 hour and filtered to remove a small insoluble fraction. The organic phase is decanted and the mother liquors are extracted with ethyl acetate (2×400 cc). The organic phase is dried over sodium sulphate, filtered and treated with animal charcoal (16 to 20 g) to decolorize it, and is filtered and concentrated to dryness.

The solid residue is taken up in acetone (80 cc), stirred for 1 hour and filtered and then washed with cold acetone (2×15 cc). The treatment in acetone is repeated once to give a beige-yellow crystalline powder (6.3 g), m.p. =216-218° C., corresponding to 1-[(3-dimethylamino)propyl]amino-9-hydroxy-4-methyl-5H-pyrido [4,3-b]benzo[e]indole.

1-[(3-Dimethylamino)propyl]amino-9-hydroxy-4-methyl-5H-pyrido [4,3-b]benzo[e]indole (7.5 g) in solution in boiling methyl ethyl ketone (650 cc) is added to a solution of methanesulphonic acid (6.4 g, 3 equivalents) in boiling methyl ethyl ketone (300 cc) and the mixture is kept under reflux for 5 minutes. An insoluble resinous mass forms, which gradually breaks up into a grey powder over 18 hours with stirring. The solid is filtered off, washed with methyl ethyl ketone and quickly put in a desiccator containing phosphorus pentoxide. After 18 hours under reduced pressure (15 mm Hg) 1-[(3-dimethylamino)propyl]amino-9-hydroxy-4-methyl-5H-pyrido [4,3-b]benzo[e]indole dimethanesulphonate (11.7 g, 97%) is obtained, m.p. =245-255° C.

A solution of 1-[(3-dimethylamino)propyl]amino-9-hydroxy-4-methyl-5H-p-yrido [4,3-b]benzo[e]indole (670 mg) in boiling methanol (150 cc) is poured into methanol (100 cc) saturated with hydrochloric acid. The solution is concentrated to 30 cc and acetone (60 cc) is added. The precipitate is filtered off after 15 minutes in the cold, washed with acetone and quickly placed in a desiccator under vacuum. Microcrystals of 1-[(3-dimethylamino)-propyl]amino-9-hydroxy-4-methyl-5H-pyrido [4,3-b]-benzo[e]indole dihydrochloride hydrate (1.5H2O) (620 mg, 72%) are thus obtained, m.p. =250-260° C. with decomposition.

1-[(3-Dimethylamino)propyl]amino-9-hydroxy-4-methyl-5H-pyrido [4,3-b]benzo[e]indole (350 mg) in solution in boiling acetone (100 cc) is poured into a solution of maleic acid (350 mg, 3 equivalents) in boiling acetone (30 cc) and the mixture is left in a stoppered flask overnight at room temperature. The solid obtained is filtered off, washed with acetone and placed for 18 hours under vacuum to give beige microcrystals of 1-[(3-dimethylamino)propyl]amino-9-hydroxy-4-methyl-5H-pyrido [4,3-b]benzo[e]indole dimaleate, m.p. =204-206° C.

1-[(3-Dimethylamino)propyl]amino-9-methoxy-4-methyl-5H-pyrido [4,3-b]benzo[e]indole may be prepared in the following manner:

1-Chloro-9-methoxy-4-methyl-5H-pyrido [4,3-b]benzo[e]indole (7.2 g, 24 mmol) is placed in a 500-cc flask containing a large excess of 3-dimethylaminopropylamine (120 cc) and is heated under reflux, under nitrogen and with stirring, for 72 hours (complete disappearance of the chloro derivative, checked on a silica plate).

The excess diamine is evaporated off on a water bath under reduced pressure and the residue is taken up in water and then made alkaline with aqueous ammonia. The solid formed is filtered off, washed with water, taken up in methylene chloride and washed with water (150 cc) to which aqueous ammonia (10 cc) has been added.

The organic solution is dried, filtered and evaporated to give a solid residue corresponding to pure (TLC) 1-[(3-dimethylamino)propyl]amlno-9-methoxy-4-methyl-5H-pyrido [4,3-b]benzo[e]indole (8.7 g).

1-Chloro-9-methoxy-4-methyl-5H-pyridoi4,3-b]-benzo [e]indole may be obtained in the following manner:

9-Methoxy-4-methyl-2H,5H-pyrido[4,3-b]benzo[e]-1-indolone (12.2 g, 43 mmol), acetamide (10.4 g, 172 mmol), benzyltriethylammonium chloride (40 g, 172 mmol), acetonitrile (110 cc) and freshly rectified diethylaniline (28 cc, 172 mmol) are introduced into a 1-liter round bottom flask fitted with a magnetic stirrer, a dropping funnel, a condenser and kept under nitrogen.

Rectified phosphorus oxychloride (200 cc) is added progressively via the funnel and an exothermic reaction is observed. The mixture is heated under reflux for 10 hours, while a precipitate appears after it has passed through a homogeneous stage. After the time shown it is concentrated to dryness on a water bath heated to 70° C. and under reduced pressure (15 mm Hg).

Ice water (300 cc) is added to the residue obtained and the mixture, stirred well for 2 minutes, is heated to boiling. A yellow precipitate forms, which is filtered off cold and then washed with cold water. This precipitate is taken up in distilled water (300 cc) and the mixture is made alkaline, cold, with aqueous ammonia. The whole is left stirring for 1 hour and the precipitate is filtered off and washed with water. The check by thin layer chromatography shows the presence of the expected compound ($R_f$=0.5) and the presence of traces of the starting compound ($R_f$=0.36) ($SiO_2$, 9/1 $CH_2Cl_2$—EtOH). The expected product crystallizes from alcohol, in which it is very poorly soluble (large volumes) to give yellow needles (12 g, 92%), m.p.>270° C. (rf=0.58 on silica plate, pure ethyl acetate eluent).

9-Methoxy-4-methyl-2H,5H-pyrido[4,3-b]benzo[e]indol-11-one can be prepared in the following manner:

N-4-(5-Methyl-1H-2-pyridonyl)N,-2-(6-methoxy-1,2,3,4-tetrahydronaphthalenylidene)hydrazine (31 g, 0.1 mol) and diphenyl ether (1 liter) are mixed in a 4-liter three-necked flask and are then heated under reflux for 40 minutes while the whole is kept well stirred and under nitrogen. The mixture becomes homogeneous and the color fades. Heating is stopped by allowing to cool to 200° C. and checking the conversion of the starting compound. While stirring is continued, charcoal containing 10% palladium (5 g) suspended in diphenyl ether (100 cc) is added progressively, with precautions (foaming and hydrogen release) and the new mixture is again heated under reflux for 40 minutes. Hexane (2 liters) is added to the cooled mixture and the precipitate formed is filtered off and then washed with hexane. It is then taken up in boiling acetic acid (1 liter), filtered to remove the palladized charcoal and the latter is washed once with boiling acetic acid (50 to 100 cc). The combined filtrate is concentrated to 500 cc and the solid obtained after cooling is filtered off, washed with boiling acetone and dried to give pale yellow microcrystals (22 g, 75%), m.p.=260° C., corresponding to the expected 9-methoxy-4-methyl-2H,5H-pyrido[4,3-B]benzo[E]indol-1-one, slightly hydrated (rf =0.36 on silica plate with a 9/1 $CH_2Cl_2$—EtOH mixture as eluent).

N-4-(5-Methyl-1H-2-pyridonyl),N'-2-(6-methoxy-1,2,3,4-tetrahydronaphthalenylidene) hydrazine can be prepared in the following manner:

The mixture of 4-hydrazino-5-methyl-1H-2-pyridone (13.9 g, 0.1 mol) in absolute ethanol (600 cc) is heated to reflux. 6-Methoxy-2-tetralone (11.3 g, 0.12 mol) is added to the solution which has become homogeneous on boiling, and the mixture, which rapidly becomes heterogeneous, is heated under reflux for 4 hours 30 minutes. The precipitate formed is filtered off, is taken up in boiling ethanol (400 cc), in which the hydrazone is very poorly soluble and is then filtered cold to give colorless microcrystals (15.7 g, 98%), m.p.=240-250° C. with decomposition.

EXAMPLE 2

(R,S)-1-(3-Dimethylamino-2-methylpropyl)amino-9-methoxy-4-methyl-5H-pyrido [4,3-b]benzo[e]indole dimaleate (3 g) is dissolved in water and aqueous ammonia is added to it. After extraction with methylene chloride (3×100 cc), drying and concentration to dryness, the corresponding free base is obtained, which is employed in this form in the following synthesis.

(R,S)-1-(3-Dimethylamino-2-methylpropyl)amino-9-methoxy-4-methyl-5H-pyrido [4,3-b]benzo[e]indole is taken up in hydrobromic acid (120 cc, d=1.47, 47%) by operating in a manner similar to Example 1.

After heating under reflux for 4 hours and cooling a precipitate appears. The reaction mixture is concentrated to dryness under reduced pressure, water (200 cc) is then added to the residue, and the solution obtained is filtered to remove a small quantity of insoluble material. Triethylamine (20 cc) and concentrated aqueous ammonia (30 cc) are added to the filtrate, followed by methylene chloride (200 cc). After stirring for 1 hour at room temperature, the mixture is extracted with methylene chloride (4×100 cc), is dried and is concentrated to dryness.

The solid residue is chromatographed on alumina, elution being carried out successively with methylene chloride (500 cc), a 97-3 mixture of methylene chloride and ethanol (1 liter) and an 80-20 mixture of methylene chloride and ethanol (1 liter). The fractions corresponding to the last liter of eluent are collected and concentrated to dryness. Crude (R,S)-1-(3-dimethylamino-2-methylpropyl)amino-9-hydroxy-4-methyl-5H-pyrido [4,3-b]benzo[e]indole (2.1 g) is thus obtained.

The product obtained is dissolved in acetone (200 cc) and heated to boiling and maleic acid (2.1 g, 3 equivalents) in solution in boiling acetone (50 cc) is then added to it. The mixture is concentrated to half its volume and allowed to cool. (R,S)-1-(3-Dimethylamino-2-methylpropyl)amino-9-hydroxy-4-methyl-5H-pyrido [4,3-b]benzo[e]indole dimaleate (2.25 g), melting at 215–220° C., is thus obtained.

(R,S)-1-(3-Dimethylamino-2-methylpropyl)-amino-9-methoxy-4-methyl-5H-pyrido [4,3-b]benzo[e]indole dimaleate can be obtained in the following manner:

1-Chloro-9-methoxy-4-methyl-5H-pyrido [4,3-b]benzo[e]indole (2.1 g) is heated with 3-dimethylamino-2-methylpropylamine to 180° C. in an autoclave for 16 hours.

The operation is carried out in the conditions described in Example 1, the mixture is made alkaline with aqueous ammonia, is taken up with methylene chloride and is chromatographed on alumina, eluting with methylene chloride (1.5 liters). After concentration to dryness, the residue obtained is dissolved in acetone (60 cc) and heated for 2 minutes with maleic acid (2.5 g, 3 equivalents) dissolved in acetone (50 cc). After cooling and precipitation, (R,S)-1-(3-dimethylamino-2-methylpropyl) amino-9-methoxy-4-methyl-5H-pyrido [4,3-b]benzo[e]indole dimaleate (3.2 g), melting at 180° C., is obtained.

EXAMPLE 3

By using a procedure similar to Example 2, but starting with 1-[(3-dimethylamino)propyl]amino-9-methoxy-4,5-dimethylpyrido [4,3-b]benzo[e]indole trimethanesulphonate hydrate (2H2O), 1-[(3-dimethylamino)propyl]amino-9-hydroxy-4,5-dimethyl-pyrido [4,3-b]benzo[e]indole dimethanesulphonate hydrate (1.5H2O), m.p.=135–150° C., is obtained in a 95% yield.

1-[(3-Dimethylamino)propyl]amino-9-methoxy-4,5-dimethylpyrido [4,3-b]benzo[e]indole trimethanesulphonate hydrate (2H2O) can be obtained as described in Example 2, but starting from 1-chloro-9-methoxy-4,5-dimethylpyrido[4,3-b]-benzo [e]indole. The product is obtained in an 86% yield, m.p.=115–125° C.

1-Chloro-9-methoxy-4,5-dimethylpyrido[4,3-b]-benzoe [e]indole can be obtained in the following manner:

1-Chloro-9-methoxy-4-methyl-5H-pyrido[4,3-b]-benzo [e]indole (15 mmol) is dissolved in dimethylformamide (100 cc) and treated with methyl iodide (1.15 cc, 18 mmol) in the presence of potassium carbonate (16.6 g, 120 mmol) at room temperature with stirring for 15 hours. The reaction mixture is concentrated to dryness under reduced pressure.

The residue is taken up in water and extracted with methyleno chloride. The solution is dried over magnesium sulphate and concentrated to dryness. The solid residue is recrystallized from ethanol to give 1-chloro-9-methoxy-4,5-dimethyl-pyrido [4,3-b]benzo[e]indole in the form of white needles in an 86% yield; m.p. =185–187° C.

EXAMPLE 4

1-[(2-Dimethylamino)ethyl]amino-9-methoxy-4-methyl-5H-pyrido [4,3-b]benzo[e]indole is placed in a 250-cc round bottom reaction flask fitted with a stirrer and kept under nitrogen, with hydrobromic acid (80 cc, d=1.47, 47%).

This mixture, which has become homogeneous on boiling, is heated under reflux for 5 hours and is concentrated to dryness under reduced pressure. The solid residue is dissolved in water (400 cc), and made alkaline with 28% strength aqueous ammonia (18 cc), which is added dropwise, to form a resinous precipitate.

Ethyl acetate (200 cc) is added to the resulting mixture, and the whole is stirred overnight and filtered. The organic phase is separated off and the mother liquors are extracted with ethyl acetate (2×100 cc). The organic phase is dried over sodium sulphate, is filtered, treated with animal charcoal (4 g) to decolorize it, is filtered again and is concentrated to dryness.

The solid residue is taken up in acetone (30 cc) and absolute ethanol (50 cc), and the homogeneous mixture is filtered hot into a solution of maleic acid (3 equivalents) in absolute ethanol (30 cc) to give, after evaporating the solvent and taking up the residue in acetone, 1-[(2-dimethylamino)ethyl]amino-9-hydroxy-4-methyl-5H-pyrido [4,3-b]benzo[e]indole dimaleate, m.p. =210° C. The yield for the three stages: substitution, demthylation and conversion into salt is 76%.

1-[(2-Dimethylamino)ethyl]amino-9-methoxy-4-methyl-5H-pyrido [4,3-b]benzo[e]indole can be prepared in the following manner:

1-Chloro-9-methoxy-4-methyl-5H-pyrido[4,3-b]-benzo [e]indole (2 g) is placed in a 50-cc round bottom flask containing 2-dimethylaminoethylamine (20 cc, a large excess) and is heated under reflux (120° C.) under nitrogen and with stirring for 16 days (complete disappearance of the chloro derivative, checked on silica plate).

The excess diamine is evaporated off on the boiling water bath under reduced pressure and the residue is taken up in water and then made alkaline with aqueous ammonia. The solid formed is filtered off, washed with water, taken up in methylene chloride and washed with water (150 cc) and aqueous ammonia (10 cc).

The organic solution is dried, filtered and concentrated to dryness to give a solid residue corresponding to 1-[(2-dimethylamino)ethyl]amino-9-methoxy-4-methyl-5H-pyrido [4,3-b]benzo[e]indole maleate; m.p. =184° C.

EXAMPLE 5

1-[(3-Amino)propyl]amino-9-methoxy-4-methyl-5H-pyrido [4,3-b]benzo[e]indole (1.9 g) is placed in a 250-cc round bottom reaction flask fitted with a stirrer and kept under argon, with hydrobromic acid (70 cc, d=1.47; 47%).

This mixture, which has become homogeneous on boiling, is heated under reflux for 5 hours 30 minutes and is concentrated to dryness under reduced pressure. The solid residue is dissolved in water (200 cc) and made alkaline with 28% strength aqueous ammonia (20 cc) which is added dropwise, to form a resinous precipitate.

Ethyl acetate (200 cc) and ethanol (50 cc) are added to the resulting mixture, the whole is stirred for 1 hour and is filtered to remove a small insoluble fraction. The organic phase is decanted off and the mother liquors are extracted with ethyl acetate (2×100 cc). The organic phase is dried over sodium sulphate, is filtered and treated with animal charcoal (4 g) to decolorize it and is then filtered and concentrated to dryness.

The solid residue is taken up in acetone (30 cc), stirred for 15 min. and filtered and then washed with cold acetone (2×10 cc) to give a solid (1.5 g, 80%) corresponding to 1-[(3-amino)propyl]-amino-9-hydroxy-4-methyl-5H-pyrido [4,3-b]benzo[e]indole, hydrated with 1.3 molecules of water, the dimaleate of which, recrystallized from an ethanol-acetone mixture, melts at 132–136° C.

1-[(3-Amino)propyl]amino-9-methoxy-4-methyl-5H-pyrido [4,3-b]benzo[e]indole can be prepared in the following manner:

The chloro derivative (2.5 g) is placed in a 250-cc round bottom flask (large excess) of 3-aminopropylamine and heated to 160° C. under nitrogen and with stirring for 18 hours (complete disappearance of the chloro derivative, checked on silica plate).

The excess diamine is evaporated off on the boiling water bath under reduced pressure and the residue is taken up in water and then made alkaline with aqueous ammonia. The solid formed is filtered off, washed with water and dried in the desiccator to give a solid product (2.8 g) corresponding to the expected compound.

The dimaleate, prepared in absolute ethanol in the presence of an excess of maleic acid and washed with acetone, corresponds to the monohydrated salt of 1-[(3-aminopropyl]amino-9-methoxy-4-methyl-5H-pyrido [4,3-b]benzo[e]indole; m.p.=170° C.

EXAMPLE 6

1-[(3-Dimethylamino)propyl]amino-4-ethyl-9-methoxy-5H-pyrido [4,3-b]benzo[e]indole (free base) is placed in a 250-cc round bottom reaction flask fitted with a stirrer, under argon, with hydrobromic acid (66 cc, d=1.47; 47%).

This mixture, which has become homogeneous on boiling, is heated under reflux for 5 hours and is concentrated to dryness under reduced pressure. The solid residue is dissolved in water (200 cc) and made alkaline wit 28% strength aqueous ammonia (15 cc), which is added dropwise, to form a resinous precipitate.

Ethyl acetate (200 cc) is added to the resulting mixture and the whole is stirred for one hour. The organic phase is decanted off and the mother liquors are extracted with ethyl acetate (2×100 cc). The organic phase is dried over sodium sulphate, is filtered and is treated with animal charcoal (5 g) to decolorize it and is then filtered and concentrated to dryness.

The solid residue is taken up in acetone (40 cc) and treated with maleic acid (2.5 g) in solution in boiling acetone (40 cc). 1-[(3-Dimethylamino)propyl]amino-4-ethyl-9-hydroxy-5H-pyrido [4,3-b]benzo[e]indole dimaleate (2.34 g, yld=72% for the 3 stages: substitution - demethylation - conversion to salt) is filtered off and dried to give cream-colored microcrystals; m.p.=154° C.. 1-[(3-Dimethylamino)propyl]amino-4-ethyl-9-methoxy-5H-pyrido [4,3-b]benzo[e]indole can be obtained in the following manner.

1-Chloro-4-ethyl-9-methoxy-5H-pyrido[4,3-b]-benzo[e]indole (2 g) is placed in a 250-cc round bottom flask containing 3-dimethylaminopropylamine (40 cc, large excess) and is heated under reflux, under nitrogen and with stirring, for 72 hours (complete disappearance of the chloro derivative, checked on silica plate).

The excess diamine is evaporated off on the boiling water bath under reduced pressure and the residue is taken up in water and then made alkaline with aqueous ammonia. The solid formed is filtered off, washed with water, taken up in methylene chloride and washed with water (150 cc) and aqueous ammonia (10 cc).

The organic solution is dried, filtered and evaporated down to give a solid residue corresponding to the expected 1-[(3-dimethylamino)propyl]amino-4-ethyl-9-methoxy-5H-pyrido [4,3-b]benzo[e]indole.

The corresponding dimaleate, formed in the usual conditions, melts at 154° C.

1-Chloro-4-ethyl-9-methoxy-5H-pyrido[4,3-b]-benzo[e]indole can be obtained in the following manner:

Into a 500-cc round bottom flask fitted with a magnetic stirrer, a dropping funnel, a condenser and kept under nitrogen, are introduced: 9-methoxy-4-ethyl-2H,5H-pyrido [4,3-b]benzo[e]-1-indolone (6 g) in boiling and dried ethanol, benzyl triethylammonium chloride (19.2 g), acetamide (5.1 g), acetonitrile (60 cc) and freshly rectified diethylaniline (13.2 g).

Rectified phosphorus oxychloride (96 cc) is added progressively via the funnel, and an exothermic reaction is observed. The mixture is heated under reflux for 6 hours 30 minutes, while, after having passed through a homogeneous stage, a precipitate appears. It is evaporated to dryness on the water bath heated to 70° C. and under 15-mm vacuum.

Iced water (600 cc) is added to the residue obtained and the mixture, stirred well for 2 hours, is heated to boiling. After having cooled, a yellow precipitate is obtained, which is filtered off cold and is then washed with cold water. This precipitate is taken up in distilled water (500 cc) and the mixture is made alkaline, cold, with aqueous ammonia. The whole is left stirring for 1 hour 30 minutes and the precipitate is filtered off and washed with water. It recrystallizes from alcohol, giving yellow needles (4.6 g) of 1-chloro-4-ethyl-9-methoxy-5H-pyrido[4,3-b]benzo[e]indole; m.p. =260° C. (62% yield).

9-Methoxy-4-ethyl-2H,5H-pyrido[4,3-b]benzo[e]-1-indolone can be obtained in the following manner:

N-4-(5-Ethyl-1H-2-pyridonyl)N'-2-(methoxy-1,2,3,4-tetrahydronaphthalenylidene) hydrazine (14.5 g) and diphenyl ether (350 cc) are mixed in a 1-liter three-necked flask and are then heated under reflux for 30 minutes, while the whole is kept well stirred and under nitrogen. The mixture becomes homogeneous and the color fades. Heating is interrupted to allow to cool to 200° C. and to check that the starting compound is completely converted: Merck silica plate, methylene chloride-ethanol (8/2 by volume) eluent, ($R_f$ hydrazone=0.5, $R_f$ intermediate compound=0.8). While stirring is continued, charcoal containing 10% palladium (2 g) in suspension in diphenyl ether (20 cc) is added progressively with precaution (foaming and hydrogen release), and the new mixture is heated under reflux for 30 minutes (disappearance of the intermediate compound) ($R_f$=0.35 silica-pure ethyl acetate; expected product: $R_f$=0.58). Hexane (400 cc) is added to the cooled mixture and the precipitate formed is filtered off and then washed with hexane. It is then taken up in boiling acetic acid (350 cc), is filtered to remove the palladized charcoal and the latter is washed with boiling acetic acid (2×30 cc). The combined filtrate is concentrated to 150 cc and the solid obtained after cooling is filtered off and dried under vacuum to give pale yellow microcrystals (13.7 g, quantitative yield, m.p. >260° C.) corresponding to hydrated 9-methoxy-4-ethyl-2H, 5H-pyrido[4,3-b]benzo[e]-l-indolone (m.p. >260° C.).

N-4-(5-Ethyl-1H-2-pyridonyl)N,-2-(methoxy-1,2,3,4-tetrahydronaphthalenylidene) hydrazine can be obtained in the following manner:

The mixture of 4-hydrazino-5-ethyl-1H-2-pyridone (7 g) in absolute ethanol (250 cc) is heated to reflux. 6-Methoxy-2-tetralone (9/3 g) is added to the solution, which has become homogeneous on boiling, and the mixture, which has quickly become heterogeneous, is heated under reflux for 4 hours 30 minutes (disappearance of hydrazine checked by TLC on Merck silica plate, 7/3 by volume methylene chloride-ethanol eluent, $R_f$=0.75). The precipitate formed is filtered off, taken up in ethanol (100 cc) in which the hydrazone is poorly soluble, and is then filtered cold to give colorless crystals (12.1 g, 85%) of N-4-(5-ethyl-1H-2-pyridonyl)N,-2-(methoxy-1,2,3,4-tetrahydronaphthalenylidene) hydrazine, m.p.=135–140° C., with decomposition.

4-Hydrazino-5-ethyl-1H-2-pyridone can be obtained in the following manner:

4-Hydroxy-5-ethyl-1H-2-pyridone (12 g), ethylene glycol monoethyl ether (40 cc) and hydrazine hydrate (11 cc) are mixed in a reaction flask placed under nitrogen and fitted with a magnetic stirrer and a condenser.

The whole is heated under reflux, with stirring, for 4 days in all.

After having been allowed to stand cold overnight, the solid obtained is filtered off, washed with cold absolute ethanol (10 cc) and is dried to give 4-hydrazino-5-ethyl-1H-2-pyridone monohydrate (7.8 g, 59 %), m.p.=130–132° C. with decomposition.

4-Hydroxy-5-ethyl-1H-2-pyridone is described by M. Legraverend, C.H. Nguyen, A. Z e,acu/e/ rial and E. Bisagni, Nucleosides and Nucleotides 5, 125–134 (1986).

The present invention also relates to pharmaceutical compositions which contain as active product at least one product of general formula (I) in the pure state (in free form or in the form of salt) or in combination with one or more pharmaceutically acceptable adjuvants. These compositions may be employed parenterally.

The compositions for parenteral administration may be aqueous or nonaqueous sterile solutions, suspensions or emulsions. Propylene glycol, a polyethylene glycol or vegetable oils, in particular olive oil, and injectable organic esters, for example ethyl oleate, can be employed as a solvent or carrier. These compositions may also contain adjuvants, in particular wetting agents, emulsifiers or dispersants. The sterilization can be carried out in various ways, for example with the aid of a bacteriological filter, by incorporating sterilizing agents in the composition, by irradiation or by heating. They can also be prepared in the form of sterile solid compositions which will be dissolved at the time of use in sterile water or any other injectable sterile medium.

In human therapeutics the medications according to the present invention are particularly useful in the treatment of digestive cancers, of pulmonary cancers, of cancers of the testicles or ovaries, and in the treatments of cancers of the head and of the neck.

In general, the medical practitioner will determine the posology which he or she considers the most appropriate as a function of the age, the weight and all the other factors pertaining to the individual to be treated.

The preferred method of administration is the intravenous route. By way of guidance, the medications according to the invention may be administered in man at a rate of 30 to 200 mg/m² per treatment, intravenously.

The following example, given without any limitation being implied, illustrates a composition according to the present invention:

EXAMPLE

A solution containing 1-[(3-dimethylamino)propyl]-amino-9-hydroxy-4-methyl-5H-pyrido [4,3-b]benzo[e]indole dihydrochloride hydrate (l.5H2O) (6.44 g) is prepared by dissolving this product in pyrogen-free physiological solution in sufficient quantity to obtain 100 cc.

The solution obtained is distributed aseptically into ampules at a rate of 2 cc per ampule. The ampules are sealed and each contains 100 mg of 1-[(3-dimethylamino)propyl]amino-9-hydroxy-4-methyl-5H-pyrido [4,3-b]benzo[e]indole.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A pyridobenzoindole derivative of formula:

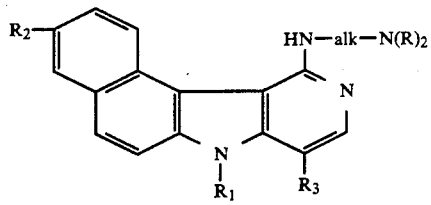

in which

R denotes a hydrogen atom or an alkyl radical containing 1 or 2 carbon atoms, alk denotes a straight or branched alkylene radical containing 2 to 4 carbon atoms, $R_1$ denotes a hydrogen atom or an alkyl radical containing 1 or 2 carbon atoms, $R_2$ denotes a hydroxyl or methoxy radical, and $R_3$ denotes an alkyl radical containing 1 or 2 carbon atoms, and its salts of addition with acids and including its hydrates and its isomeric forms and mixtures thereof.

2. The pyridobenzoindole derivative according to claim 1, wherein:

R is a hydrogen atom or a methyl radical, alk is a straight or branched alkylene radical containing 2 to 4 carbon atoms, $R_1$ is a hydrogen atom or a methyl radical, $R_2$ is the hydroxyl radical and $R_3$ is a methyl or ethyl radical, and its salts and including its hydrates and its isomeric forms and mixtures thereof.

3. The pyridobenzoindole derivative according to claim 1, wherein:

R is a methyl radical, alk is a straight o branched alkylene radical containing 2 to 4 carbon atoms, $R_1$ is a hydrogen atom or a methyl radical, $R_2$ is a hydroxyl radical, and $R_3$ is a methyl radical, and its salts and including its hydrates and its isomeric forms and mixtures thereof.

4. 1-[(3-Dimethylamino)propyl]amino-9-hydroxy-4-methyl-5H-pyrido [4,3-b]benzo[e]indole, and its salts and its hydrated forms.

5. 1-(3-Dimethylamino-2-methylpropyl)amino-9-hydroxy-4-methyl-5H-pyrido [4,3-b]benzo[e]indole, and its salts, its hydrated forms and its isomeric forms and mixtures thereof.

6. A pharmaceutical composition which contains a product according to claim 1 in the pure state or in the form of combination with any compatible and pharmaceutically acceptable diluent or adjuvant.

* * * * *